(12) United States Patent
Malloy et al.

(10) Patent No.: US 7,256,047 B2
(45) Date of Patent: *Aug. 14, 2007

(54) MEASUREMENT OF GLUCONEOGENESIS AND INTERMEDIARY METABOLISM USING STABLE ISOTOPES

(75) Inventors: Craig R. Malloy, Dallas, TX (US); A. Dean Sherry, Dallas, TX (US); John G. Jones, Coimbra (PT)

(73) Assignee: Board of Regents, The University of Texas System, Austin, TX (US)

( * ) Notice: Subject to any disclaimer, the term of this patent is extended or adjusted under 35 U.S.C. 154(b) by 1091 days.

This patent is subject to a terminal disclaimer.

(21) Appl. No.: 09/846,727

(22) Filed: May 1, 2001

(65) Prior Publication Data

US 2003/0148533 A1 Aug. 7, 2003

(51) Int. Cl.
*G01N 23/02* (2006.01)
(52) U.S. Cl. .......................... 436/56; 436/57; 436/173; 435/14; 435/72; 435/105
(58) Field of Classification Search ................ 436/56, 436/57, 173; 435/14, 72, 105
See application file for complete search history.

(56) References Cited

U.S. PATENT DOCUMENTS

| | | | | |
|---|---|---|---|---|
| 5,254,730 A | * | 10/1993 | Kilgore | 562/575 |
| 5,302,520 A | * | 4/1994 | Goux | 435/94 |
| 5,413,917 A | | 5/1995 | Malloy et al. | 435/35 |
| 5,439,803 A | * | 8/1995 | Ross et al. | 435/14 |
| 5,597,548 A | | 1/1997 | Sherry et al. | 424/9.3 |
| 5,817,474 A | * | 10/1998 | Brown | 435/29 |
| 5,910,403 A | * | 6/1999 | Hellerstein | 435/4 |
| 5,951,473 A | | 9/1999 | Sherry et al. | 600/420 |
| 6,329,208 B1 | * | 12/2001 | Jones et al. | 436/173 |
| 6,642,059 B2 | * | 11/2003 | Chait et al. | 436/173 |
| 6,764,817 B1 | * | 7/2004 | Schneider | 435/4 |

OTHER PUBLICATIONS

Magnusson et al. "Noninvasive Tracing of Krebs Cycle Metabolism in Liver," Journal of Biological Chemistry, vol. 266, No. 11, pp. 6975-6984 (1991).*
Jones et al. "An integrated 2H and 13C NMR study of gluconeogenesis and TCA cycle flux in humans," Am. J. Physiol. Endocrinol. Metab. 281: E848-E856, (2001).*
Magnusson et al. "Increased Rate of Gluconeogenesis in Type II Diabetes Mellitus," J. Clin. Invest. vol. 90, pp. 1323-1327, (1992). □□*

(Continued)

*Primary Examiner*—Monique T. Cole
(74) *Attorney, Agent, or Firm*—Gardere Wynne Sewell LLP (57) ABSTRACT

The present invention provides a combination of carbon-13 and deuterium metabolic tracers and methods that when used in conjunction with nuclear magnetic resonance spectroscopy, provide a measurement of metabolic fluxes in the target organisms. The tracers of the present invention may be taken orally during the same clinical exam. The metabolic information can be derived from blood, urine or other fluids to provide a comprehensive profile of glucogenic metabolism. The subject matter of the present invention may be applied to the study of metabolic dysfunction related to obesity, diabetes, HIV infection and a variety of other disease conditions.

31 Claims, 7 Drawing Sheets

OTHER PUBLICATIONS

Consoli et al. "Determination of Krebs Cycle Metabolic Carbon Exchange In Vivo and Its Use to Estimate the Individual Contributions of Gluconeogenesis and Glycogenesis to Overall Glucose Output in Man," J. Clin. Invest., vol. 80, pp. 1301-1310, (1987).*

Schumann et al. "Metabolism of 2-14C Acetate and Its Use in Assessing Hepatic Krebs Cycle Activity and Gluconeogenesis," J. Biol. Chem., vol. 266, No. 11, pp. 6985-6990, (1991).*

Landau et al. "Use of 2H20 for Estimating Rates of Gluconeogenesis," J. Clin. Invest., vol. 95, pp. 172-178, (1995).*

Sunehag et al. "Gluconeogenesis in Very Low Birth WEight Infants Receiving Total Parenteral Nutrition," Diabetes, vol. 48, pp. 791-800, (1999).*

J.G. Jones, et al; 13C NMR Measurements of Human Gluconeogenic Fluxes After Ingestion of (U-13C) Propionate, Phenylacetate, and Acetaminiophen; *American Journal of Physiology*; Part I of Two Parts, pp. E843-E852; Nov. 1998.

n

* cited by examiner

MEASUREMENT OF GLUCONEOGENESIS AND INTERMEDIARY METABOLISM USING STABLE ISOTOPES

The United States Government may own certain rights in this invention under National Institutes of Health Resources Grant No.: RR-02584. The liver plays a principal role in glucose homeostasis by regulating glucose synthesis and storage in response to the normal changes in daily nutritional and hormonal status. Under postabsorptive conditions, both hepatic glylogenolysis and gluconeogenesis contribute to endogenous glucose production.

FIELD OF THE INVENTION

The present invention relates generally to the field of measurement of metabolic function and specifically to the in vivo measurement using nuclear magnetic resonance spectroscopy.

BACKGROUND OF THE INVENTION

Figure 1:
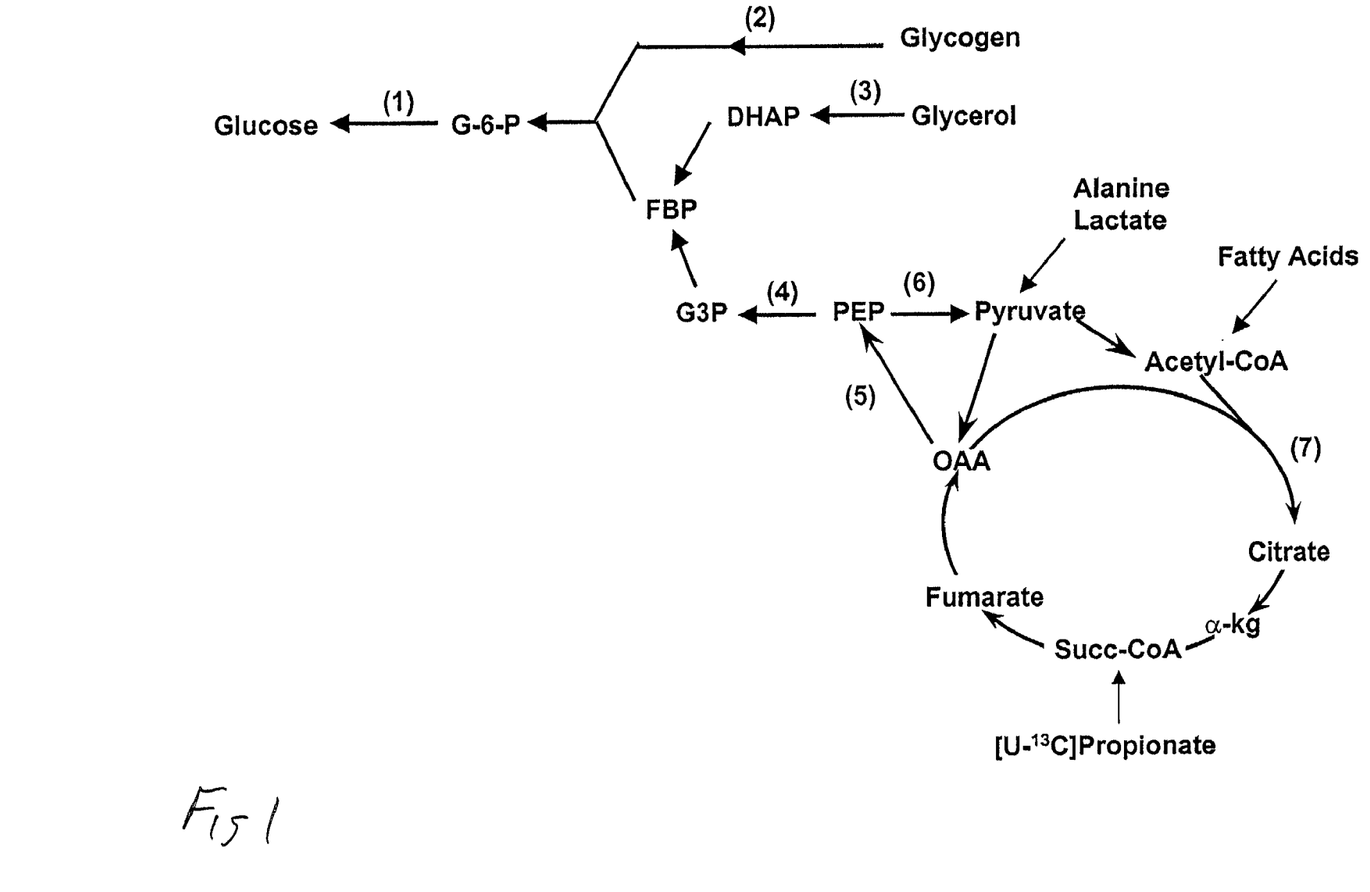
FIG. 1 depicts metabolic pathways relevant to the present invention.

Since the majority of gluconeogenic carbons are derived from phosphoenolpyruvate (PEP) via the Krebs TCA cycle, hepatic glucose production is also intimately linked to acetyl-CoA oxidation and energy production. Together, these biochemical pathways form a metabolic network, as depicted in FIG. 1, that is highly responsive to matching the external demand for glucose with the availability of glycogen, gluconeogenic precursors and energy. Measurements of carbon flux through this network typically combine an isotope dilution measurement of endogenous glucose production (GP) with additional tracer measurements of the contributing pathways.

As one example, GP in fasting humans has been determined by analysis of the $^2$H-enrichment at glucose C6 using the hexamethylenetetramine (HMT) method and mass spectrometry after infusion of [6,6-$^2$H$_2$] glucose at a known rate. It is possible to also give oral $^2$H$_2$O and measure the contribution of gluconeogenesis to glucose production from $^2$H-enrichments at glucose C5 versus C2 after parallel selective degradations of plasma glucose and analysis by mass spectroscopy. However, the contributions of glycerol versus TCA cycle intermediates to gluconeogenesis cannot be differentiated by this method nor can $^{13}$C tracers be combined with $^2$H tracers using the HMT method.

$^{13}$C tracers have also been used to measure metabolic flux through the network. Endogenous glucose production has been monitored with [U—$^{13}$C$_6$] glucose by following disappearance of the parent m+6 isotopomer from plasma glucose. Additional metabolic information has been derived from partially-labeled glucose molecules generated by recycling of $^{13}$C-label with this method. However, the extent to which the recycled label can be reliably analyzed and related to rates of gluconeogenesis and TCA cycle flux is questionable.

Others have used tracers like [3-$^{13}$C] lactate that enter at the level of the TCA cycle along with a separate tracer for measuring endogenous glucose production. Neither [U—$^{13}$C$_6$]glucose or [3-$^{13}$C]lactate tracers, however, can differentiate glucose produced from glycogen, glycerol or the TCA cycle.

SUMMARY OF THE INVENTION

The present invention provides a combination of carbon-13 and deuterium metabolic tracers and methods that when used in conjunction with nuclear magnetic resonance spectroscopy, provide a measurement of metabolic fluxes in the target organisms.

The tracers of the present invention may be taken orally during the same clinical exam. The metabolic information can be derived from blood, urine or other fluids to provide a comprehensive profile of glucogenic metabolism. The subject matter of the present invention may be applied to the study of metabolic dysfunction related to obesity, diabetes, HIV infection and a variety of other disease conditions as well as physiological events such as exercise, and the effects of drugs.

The present invention provides a comprehensive analysis of metabolic function. Other methods, such as radionuclide methods and mass spectrometric methods are not practical for such determinations and do not allow for the simultaneously use of both carbon-13 and deuterium tracer probes.

One form of the present invention is a method for preparing an tracer composition including the steps of obtaining a $^{13}$C labeled Krebs cycle metabolite and mixing the $^{13}$C labeled Krebs cycle metabolite with labeled water wherein gluconeogenesis is measured from a subject that was provided the labeled mixture by comparison of the relative nuclear magnetic resonance profiles of the labeled components.

Another form of the present invention is a method for preparing an isotopic metabolic flux tracer composition including the steps of providing a $^{13}$C labeled Krebs cycle metabolite with labeled water to a subject and obtaining a sample from the subject, followed by measuring the nuclear magnetic resonance of the labeled tracers to determine the rate of gluconeogenesis.

Yet another form of the present invention is reagent kit for use in effecting a simultaneous assay for gluconeogenesis in a sample. The reagent kit is made up of a $^{13}$C labeled Krebs cycle tracer and a labeled water tracer.

Still another form of the present invention is a method for determining gluconeogenesis made up of the steps of providing a patient with a $^{13}$C labeled Krebs cycle metabolite and D$_2$O, followed by obtaining a sample a blood, urine or tissue sample from the patient. Next, the $^2$H signal nuclear magnetic resonance spectra, $^1$H NMR nuclear magnetic resonance spectra, and the $^{13}$C—carbon nuclear magnetic resonance spectra of the sample are obtained. The data are then used to calculate the rate of gluconeogenesis by taking the known infusion rate of a $^{13}$C radiolabelled Krebs cycle metabolite divided by the average fraction found in the sample over a predetermined period.

BRIEF DESCRIPTION OF THE DRAWINGS

The above and further advantages of the invention may be better understood by referring to the following detailed description in conjunction with the accompanying drawings in which corresponding numerals in the different figures refer to the corresponding parts in which:

FIG. 2 depicts nuclear magnetic resonance spectra consistent with the present invention;

DETAILED DESCRIPTION OF THE INVENTION

While the making and using of various embodiments of the present invention are discussed herein in terms of a measuring glucogenesis in humans, it should be appreciated that the present invention provides many applicable inventive concepts that can be embodied in a wide variety of specific contexts. The specific embodiments discussed herein are merely illustrative of specific ways to make and use the invention and are not meant to limit the scope of the invention in any manner.

$^2$H NMR spectrum of monoacetone glucose may be used to measure the distribution of deuterium in blood glucose after ingestion of $^2$H$_2$O. This information allows the direct calculation of the contribution of glycogen, glycerol, and the TCA cycle to glucose production in humans.

The NMR method offers several advantages over mass spectroscopic analysis of glucose $^2$H-enrichment. First, it does not require carbon-by-carbon degradation of glucose; rather, the relative $^2$H-enrichment at each carbon position of glucose can be read out in a single $^{2H}$ NMR spectrum. Second, the prochiral H6R and H6S resonances are well separated in the $^2$H NMR spectrum of monoacetone glucose so the normal assumptions required by mass spectrometry to quantitatively evaluate exchange at the level of fumarase in the TCA cycle are eliminated. This allows a separate measure of gluconeogenesis from the level of the triose phosphates (glycerol) versus PEP (the TCA cycle). Finally, the $^2$H measurement is not compromised by the presence of $^{13}$C-tracers so experiments can be designed to measure glucose production, gluconeogenic flux, pyruvate recycling flux and TCA cycle flux in a single experiment.

The method of the present invention has been used, for example, to measure metabolic flux values in 16 hr fasted humans using the combined tracers, [1,6-$^{13}$C$_2$] glucose, $^2$H$_2$O and [U—$^{13}$C$_3$]propionate. With the use of the present method, a comprehensive picture of liver metabolism may be obtained during a single patient visit, making the technique highly suitable for routine clinical application.

EXAMPLES

Materials

99% $^2$H$_2$O, 99% [1,6-$^{13}$C$_2$]glucose, 99% [U—$^{13}$C$_3$] propionate were obtained from Cambridge Isotopes (Cambridge, Mass.). Acetaminophen was from regular strength Tylenol capsules and phenylacetate was from Sigma (St. Louis, Mo.).

Patient Protocol

Five healthy, non-obese subjects (two male and three female; ages 21-36 years; weights ranged from 50-86 kg (70±14)) were studied under a protocol approved by the institutional human studies committee.

Subjects were admitted to the General Clinical Research Center (GCRC) at Parkland Hospital and examined by an internist (history and physical). All had blood glucose levels in the normal range (70-110 mg/dl) and none reported a history of chronic illness or use of medications on a regular basis. All subjects began fasting at 6.00 PM. 99% $^2$H$_2$O was taken orally (2.5g/kg body water, the latter calculated as total weight times 0.6 for men or 0.5 for women) at 11.00 PM and again at 3.00 AM. 0.5% $^2$H$_2$O was given ad libitum during the remainder of the study. At 6.00 AM, subjects ingested a tablet containing 325 mg acetaminophen. Between 7.00-8.00 AM, subjects ingested tablets containing phenylacetate (20 mg/kg) and another 650 mg acetaminophen. At 8.00 AM, a 3 hr primed infusion of [1,6-$^{13}$C$_2$] glucose (167 mg, 1.67 mg/min) was initiated for each subject.

The infusion medium was prepared by dissolving 500 mg of sterile and pyrogen-free [1,6-$^{13}$C$_2$] glucose into 150 mL saline. The infusion medium was passed through a 0.22 μm filter during administration. Subjects received a 50 mL bolus of infusion medium over 2 min followed by constant infusion of 30 mL/hr.

Subjects also ingested [U—$^{13}$C$_3$]propionate (10 mg/kg, packaged into 3 gelcaps) between 8.00-9.00 AM. Also, beginning at 8.00 AM, 10 mL of blood were drawn from a contralateral vein every 20 min for 2 hr with additional draws at 2.5 and 3 hr. This amounted to 7 blood samples and a total of 70 mL whole blood per subject. Urine was also collected every hour from 8.00 AM to 2.00 PM, at which point the study was concluded.

Analytical Procedures

For each subject, an aliquot of the [1,6-$^{13}$C$_2$]glucose infusion medium was frozen and enzymatically assayed for glucose. Blood samples were chilled immediately after being drawn and centrifuged at 4° C. in heparinized tubes.

The plasma was then processed for $^{13}$C and $^1$H spectroscopy of plasma glucose by perchloric acid extraction. For $^2$H NMR analysis of positional deuterium enrichment, 2-3 plasma extracts from each subject were pooled and lyophilized to complete dryness. Glucose was converted to monoacetone glucose using the method of Landau et al. After lyophilization, the residue containing monoacetone glucose was dissolved in 0.6 mL 90% acetonitrile/10% $^2$H-depleted water plus a few grains of sodium bicarbonate and insoluble material was centrifuged and discarded.

Urine samples were treated with urease and β-glucuronidase and lyophilized. The extract was then reconstituted in 10 mL water and insoluble material was precipitated by centrifugation. The supernatant was adjusted to pH 1.0 with perchloric acid and the sample was applied to an 8-10 mL cation-exchange column (Dowex-50X8-H$^+$) followed by 40 mL of water. The column effluent was neutralized with KOH, lyophilized and resuspended in 600 μl $^2$H$_2$O. The pH was then adjusted to 8.0 with NH$_4$OH, the samples were centrifuged at 13,000 rpm with an Eppendorf centrifuge and the supernatants pipetted into 5-mm NMR tubes.

NMR Spectroscopy

Proton decoupled $^{13}$C NMR spectra of blood and urine extracts were collected using a Unity Inova 14.1 T spectrometer operating at 150.9 MHz. Free-induction decays were multiplied by a 0.1-0.2 Hz exponential function prior to Fourier transformation.

Typically, 9,000-18,000 free induction decays were summed for each blood extract and 6,000 for each urine extract resulting in collection times of 5-14 hr per extract. Proton-decoupled $^2$H NMR spectra of monoacetone glucose were acquired at 50° C. with the same probe using a 90° pulse and a sweep width of 920 Hz digitized into 992 points, giving an acquisition time of 0.512 seconds. No additional interpulse delays were used in this pulse sequence. Typically 90-100,000 scans were averaged. The data were zero-filled to 4K, multiplied by a 1 Hz exponential function to increase S/N and Fourier transformed.

$^2$H signal intensities obtained with these parameters were corrected for minor effects of differential saturation. A comparison of $^2$H signal areas in spectra collected using these standard pulsing conditions with those measured in spectra collected using a 1.0 s acquisition time (sufficient for complete relaxation) were identical to within 7%. Nevertheless, small correction factors were used to allow for partial saturation when using the 0.512 s acquisition conditions. $^1$H NMR spectra were obtained with the same spectrometer using a 5 mm indirect probe. Spectra were acquired with a 90° pulse following pre-saturation of the residual water signal and a 15 s interpulse delay. Long-range couplings between $^{13}$C—carbons 2-6 and H1α were abolished by the application of a narrow-band WALTZ-16 $^{13}$C-decoupling pulse sequence covering the 60-75 ppm region of the $^{13}$C—NMR spectrum. 256 acquisitions were collected for a total collection time of 64 min. All NMR spectra were analyzed using the curve-fitting routine supplied with the NUTS PC-based NMR spectral analysis program (Acorn NMR Inc., Fremont Calif.).

Metabolic Flux Calculations

The $^{13}$C-enrichment in the [1,6-$^{13}$C$_2$]glucose used for the infusions was verified by $^1$H NMR. The fraction of blood glucose that contained $^{13}$C in carbon one was defined as f, the area of the doublet due to $J_{CH}$ in the glucose H1 resonance relative to the total H1 resonance area (FIG. 2). The fraction of blood glucose that was [1,6-$^{13}$C$_2$]glucose relative to all glucose containing $^{13}$C in carbon one was defined as g, the doublet due to $J_{CC}$ arising from [1,6-$^{13}$C$_2$] glucose relative to the total area of the glucose C1 resonance (FIG. 2).

The fraction of [1,6-$^{13}$C$_2$] glucose in plasma glucose was calculated as fg. The values measured in spectra collected at 120, 150 and 180 min were averaged for each subject and used in the calculation of GP. The rate of appearance of glucose ($R_a$) was calculated from the known infusion rate of [1,6-$^{13}$C$_2$]glucose, r, divided by the average fraction found in plasma over the 120-180 min period. Glucose production is then defined as $R_a$ minus the rate of infusion of [1,6-$^{13}$C$_2$] glucose, or GP=(r/fg)–r.

The fraction of glucose derived from glycogen, PEP and gluconeogenesis was estimated from the ratio of deuterium enrichment at positions 2, 5 and 6S as reported in the $^2$H NMR spectrum of monoacetone glucose (42) using the following equations:

Glucose fraction from glycogen=1–(H5/H2) (1)

Glucose fraction from glycerol=(H5–H6S)/H2 (2)

Glucose fraction from PEP=H6S/H2 (3)

Relative anaplerotic flux (OAA→PEP), pyruvate recycling flux (PEP→pyruvate or equivalent pathway), and gluconeogenic flux (PEP→glucose) were calculated from the multiplet areas measured in the $^{13}$C NMR spectrum of urinary glucuronate or phenylacetylglutamine as described previously. For urinary glucuronate C5 (the C5β resonance was analyzed) the relevant equations are:

OAA→PEP=(C5D56–C5D45)/C5D45 (4)

PEP→pyruvate=(C5D56–C5Q)/C5D45 (5)

PEP→glucose=(C5Q–C5D45)/C5D45 (6)

For phenylacetylglutamine C2 the relevant equations are:

OAA→PEP=(C2D23–C2D12)/C2D12 (7)

PEP→pyruvate=(C2D23–C2Q)/C2D12 (8)

PEP→glucose=(C2Q–C2D12)/C2D12 (9)

Gluconeogenic flux from PEP is the difference between anaplerosis (OAA→PEP) and pyruvate recycling (PEP→pyruvate). PEP recycling is indicated here by PEP→pyruvate, although it should be noted that the combined pathway OAA→PEP→pyruvate cannot be distinguished from malate→pyruvate or the Cori cycle pathways.

These relative fluxes were then converted to absolute values as follows. First, absolute fluxes in hexose units from glycogen, PEP and glycerol were defined as the product of each fractional contribution (eqns 1-3) times the endogenous glucose production (GP) in units of μmol of glucose/kg/min. Second, the rate of production of glucose from PEP was converted to the rate of production of PEP by multiplying by 2. Finally, fluxes involved in the TCA cycle were calculated by indexing the relative fluxes (equations 4-6 or 7-9) to the rate of production of PEP.

For example, if glucose production is 10 μmol/kg/min and the relative sources of glucose are glycerol (4%), glycogen (50%) and PEP (46%), then the rate of production of glucose from PEP is 4.6 μmol hexose units/kg/min or 9.2 μmol triose units/kg/min. Flux ratios related to the TCA cycle are defined relative to citrate synthase. Given relative fluxes of OAA→PEP (6.5), PEP →pyruvate (5) and PEP→glucose (1.5), then flux through OAA→PEP=6.5×9.2÷1.5=39.9 μmol /kg/min, and citrate synthase flux=9.2÷1.5=6.1 μmol /kg/min.

Statistical Analysis

All results are presented as the mean ±1 standard deviation. Means were compared as noted using a t test assuming unequal variances.

Each of the three separate components required for analysis of gluconeogenesis will be presented individually.

Endogenous Glucose Production Measurement from [1, 6-$^{13}$c$_2$] glucose.

A $^{13}$C NMR spectrum of the plasma glucose C1β resonance from blood taken 180 min after administration of [U—$^{13}$C$_3$] propionate and [1,6-13C$_2$]glucose is shown in FIG. 2. The resonance features well-resolved multiplets arising from $^{13}$C-$^{13}$C splitting, reflecting the presence of multiply labeled glucose molecules. These include signals from glucose isotopomers generated from the gluconeogenic metabolism of [U—$^{13}$C$_3$]propionate (D12 and D123) in addition to the tracer amount of infused [1,6-$^{13}$C$_2$]glucose (D16). The fraction of [1,6-$^{13}$C$_2$]glucose remaining in plasma at any time can be quantified by measuring the contribution of [1,6-$^{13}$C$_2$]glucose to the C1β resonance ($^{13}$C spectrum) and the total $^{13}$C enrichment as reported in the H1α resonance ($^1$H spectrum). The $^1$H NMR spectrum of the H1α proton features well-resolved $^{13}$C-satellites with sufficient signal-to-noise for reliable quantitation of the 2-3% excess $^{13}$C-enrichment levels from this experiment.

Figure 3:
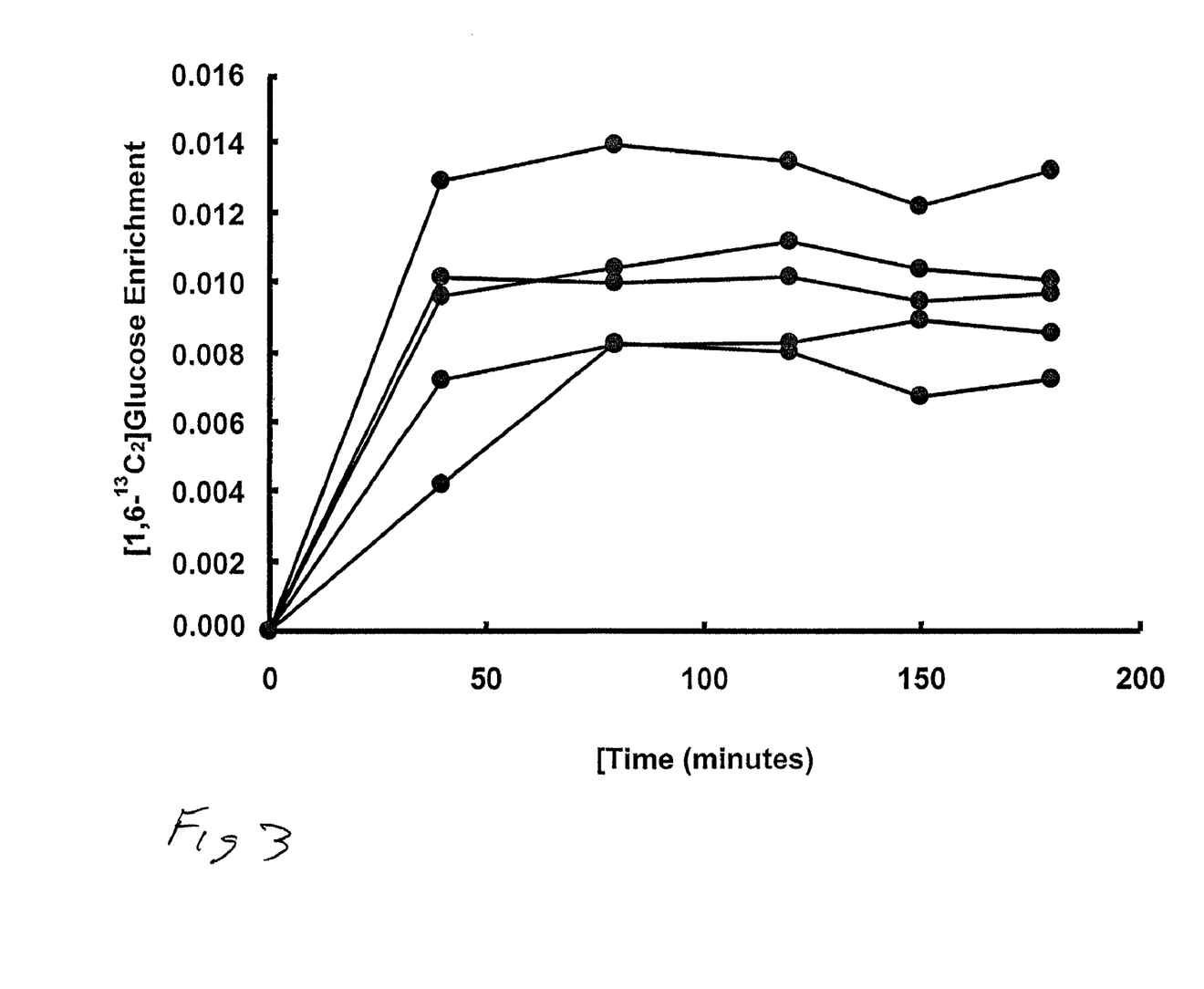
FIG. 3 depicts the time course of plasma enrichment with labeled glucose in accordance with the present invention.

FIG. 3 summarizes the [1,6-C$_2$]glucose fractional enrichment values obtained from serial blood sampling for the five subjects. The fractional enrichment of plasma [1,6-$^{13}$C$_2$] glucose reached steady-state well before the end of the infusion, with enrichments ranging from 0.75-1.35%. For each individual, the steady-state enrichment was calculated as the mean of the 120, 150 and 180 min enrichments. From these data, average endogenous GP for these five individuals was 10.7±0.9 μmol/kg/min, with a range of 9.8-12.1 μmol/kg/min. These values are in good agreement with other measures of endogenous GP in healthy individuals following similar fasting times.

Analysis of Plasma Glucose $^2$H Enrichment by $^2$H NMR

Figure 4:
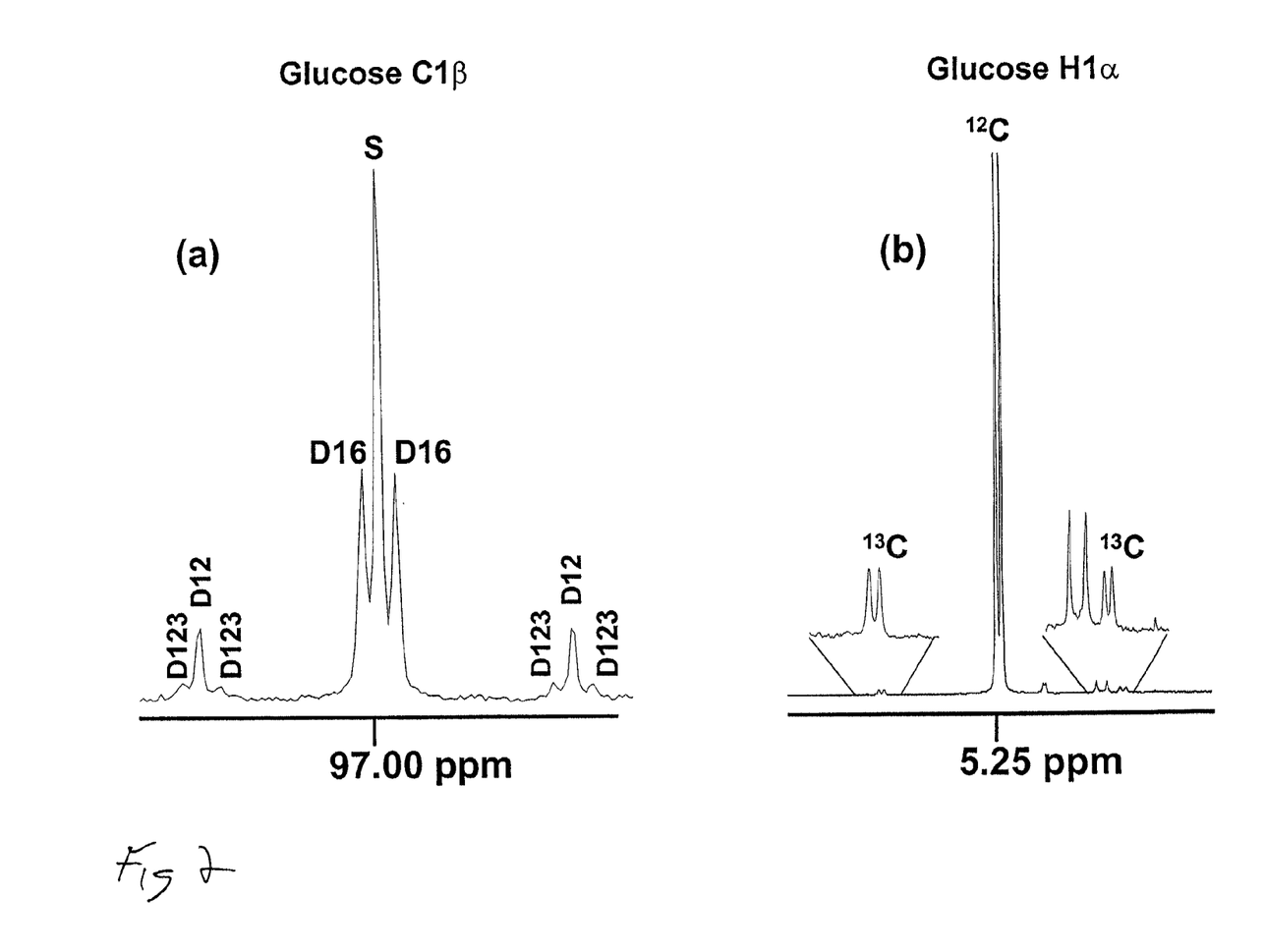
FIG. 4 depicts proton nuclear magnetic resonance spectra consistent with the present invention.

FIG. 4 shows a $^2$H NMR spectrum of monoacetone glucose derived from 2 pooled plasma extracts (corresponding to 20 mL of whole blood). The area of each resonance is proportional to $^2$H-enrichment at that position, so the spectrum provides a simple and direct readout of $^2$H enrichment ratios.

It is important to point out that the $^2$H NMR measurement is not influenced by the presence of tracer levels of $^{13}$C in the glucose (or monoacetone glucose) molecule. Table 1 summarizes the relative contributions of glycogen, glycerol and PEP to glucose production as measured by deuterium NMR of monoacetone glucose derived from blood glucose. Fluxes through key pathways involving the TCA cycle were measured relative to flux through citrate synthase by analysis of carbon-13 NMR spectra from urinary acetaminophen glucuronide or urinary phenylacetylglutamine. The equation (eqn) used to calculate a given value is indicated.

multiplets in blood glucose C2β and urinary glucuronate C5β report identical flux values and the large differences in signal-to-noise of the spectra shown, relative flux values as reported by the glucuronate spectra are reported here. Estimates of flux ratios based on acetaminophen glucuronide for five healthy, non-obese individuals were OAA→PEP=7.1±1.1; PEP→pyruvate=5.3±1.0 and PEP→glucose=1.8→0.3 (Table 1).

Figure 6:
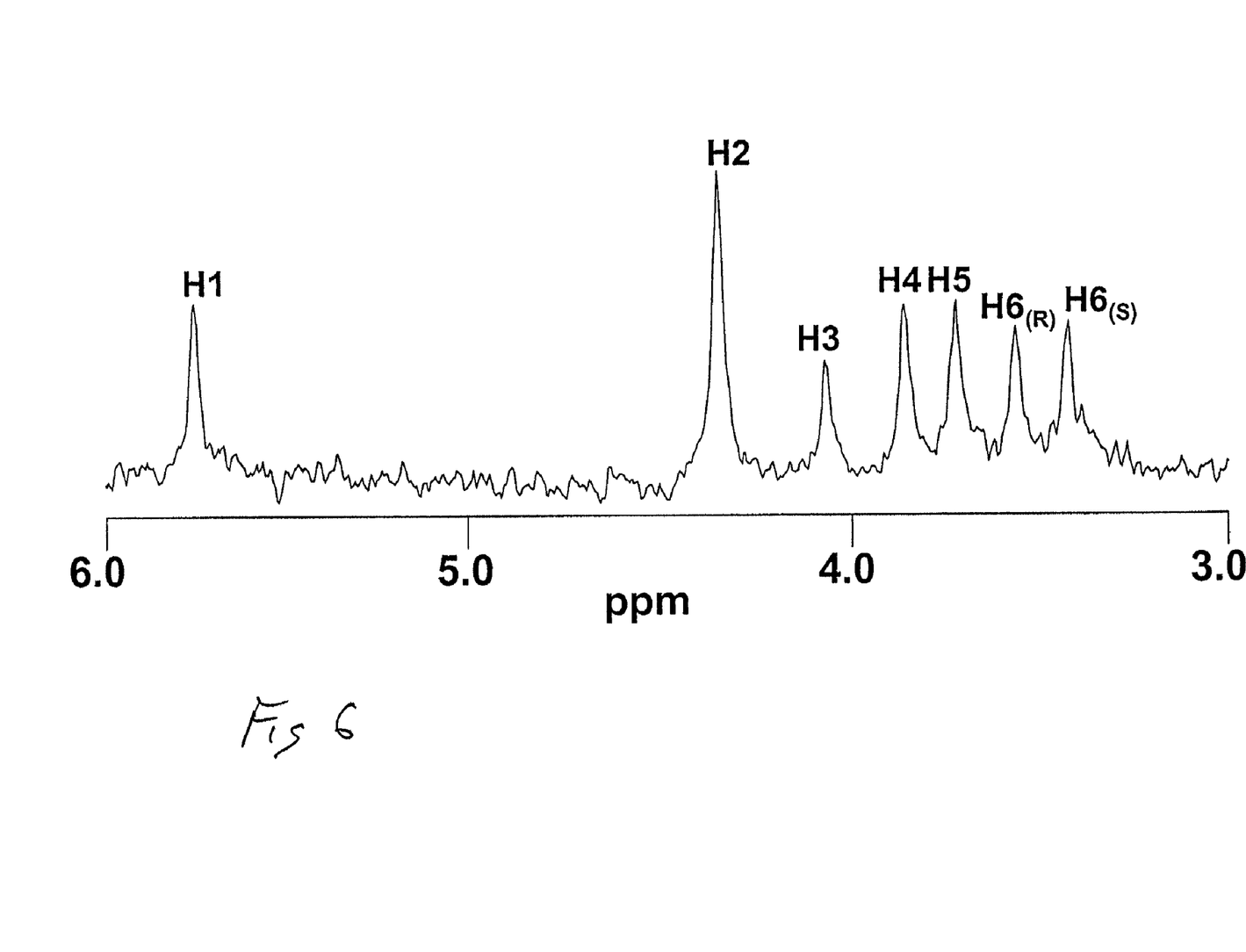
FIG. 6 depicts C-13 nuclear magnetic resonance spectra consistent with the present invention.

The $^{13}$C NMR spectra of urinary PAGN were also of high quality (FIG. 6). Analysis of the glutamine C2 multiplets using eqns 7-9 provided the following relative flux estimates (Table 1): OAA→PEP=6.3±0.4;PEP→pyruvate=5.4±0.4 and PEP →glucose=0.9±0.2. As noted in an earlier study of 24-28 hr fasted individuals (21), flux estimates determined by analysis of PAGN were significantly different from those derived from spectra of either blood glucose or urinary glucuronate. A comparison of the flux ratios derived from acetaminophen glucuronide and PAGN (Table 1) shows that PAGN reports a significantly lower relative PEP→glucose flux than reported by glucuronate (p<0.01). There was no significant difference in estimates of PEP→pyruvate or OAA→PEP (relative to citrate synthase, Table 1).

Using the methylene carbon of phenylacetate (~44 ppm, 1.1% $^{13}$C) as an internal standard, the enrichment in PAGN C2 and C3 was 2.13±0.19% and 2.04±0.16%, respectively, while the $^{13}$C enrichment in C4 was essentially equal to natural abundance levels (1.00±0.06%).

The enrichment in C4 reports enrichment in acetyl-CoA and suggests that carbon 2 of acetyl-CoA was not enriched above natural abundance. However, the PAGN C4 resonance

TABLE 1

| | Sources of glucose (fraction, from $^2$H NMR of blood monoacetone glucose) | | | Flux ratios relative to citrate synthase (from $^{13}$C NMR of urine acetaminophen glucuronide) | | | Flux ratios relative to citrate synthase (from $^{13}$C NMR of urine phenyacetylglutamine) | | |
|---|---|---|---|---|---|---|---|---|---|
| subject | glycogen (eqn 1) | glycerol (eqn 2) | PEP (eqn 3) | OAA → PEP (eqn 4) | PEP → pyruvate (eqn 5) | PEP → glucose (eqn 6) | OAA → PEP (eqn 7) | PEP → pyruvate (eqn 8) | PEP → glucose (eqn 9) |
| A | 0.57 | 0.00 | 0.43 | 6.61 | 5.18 | 1.44 | 6.58 | 5.90 | 0.69 |
| B | 0.55 | 0.06 | 0.39 | 7.41 | 5.10 | 2.31 | 6.34 | 5.44 | 0.90 |
| C | 0.43 | 0.01 | 0.56 | 5.50 | 3.76 | 1.74 | 6.15 | 5.03 | 1.12 |
| D | 0.45 | 0.06 | 0.49 | 7.51 | 5.62 | 1.89 | 6.80 | 5.73 | 1.07 |
| E | 0.59 | 0.03 | 0.38 | 8.85 | 6.68 | 1.85 | 5.66 | 4.96 | 0.70 |
| mean | 0.52 | 0.03 | 0.45 | 7.11 | 5.27 | 1.85 | 6.31 | 5.41 | 0.90 |
| s.d. | 0.07 | 0.03 | 0.08 | 1.13 | 1.05 | 0.31 | 0.44 | 0.41 | 0.20 |

TCA cycle and gluconeogenic flux measurements from [U—$^{13}$C$_3$]propionate incorporation into hexose and PAGN.

Relative anaplerotic, pyruvate recycling, and gluconeogenic fluxes can be obtained by a $^{13}$C isotopomer analysis of plasma glucose, urinary glucuronide, or the glutamine fragment in urinary PAGN. The equations that describe these relationships are given by eqns. 4-9.

Figure 5:
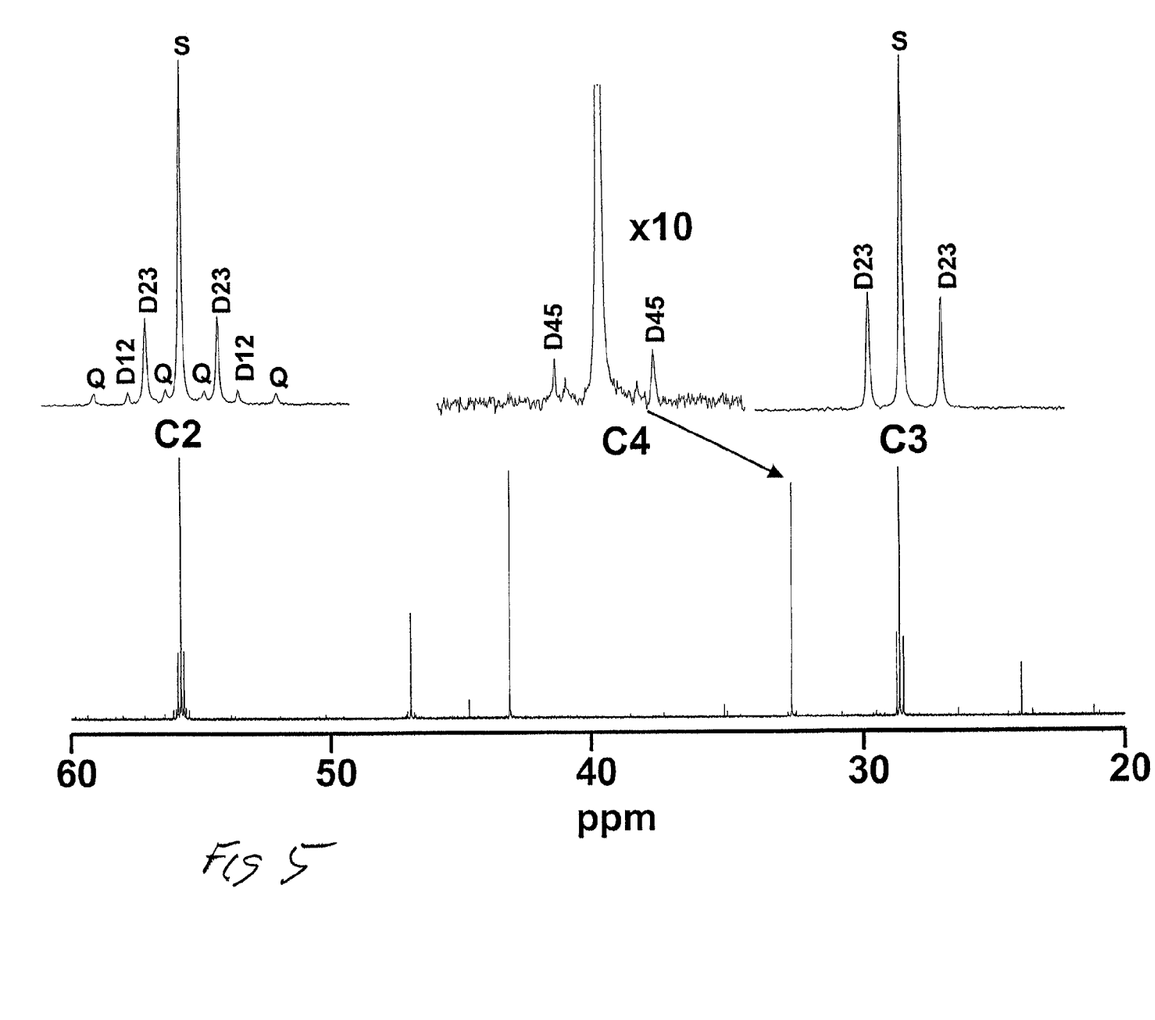
FIG. 5 depicts C-13 nuclear magnetic resonance spectra consistent with the present invention.

FIG. 5 illustrates typical multiplets observed in the $^{13}$C NMR spectrum of plasma glucose C2β and urinary glucuronate C5β of the same individual. The multiplet pattern arises from metabolism of [U—$^{13}$C$_3$]propionate at the level of the liver TCA cycle and is not affected by the presence of or metabolism of [1,6-$^{13}$C$_2$]glucose. The difference in signal-to-noise in these two spectra is largely due to the amount of urinary glucuronate in ~100-150 mL of urine compared to the amount of glucose in 10 mL of blood. Given that the did show a very small doublet (D45) characteristic of C4-C5 coupling (52 Hz) resulting from entry of [1,2-$^{13}$C$_2$]acetyl-CoA into the TCA cycle. Since [1,2-$^{13}$C$_2$]acetyl-CoA can only arise from either [1,2,3-$^{13}$ C$_3$] or [2,3-$^{13}$C$_2$] pyruvate, the presence of D45 indicates that a small portion of recycled pyruvate was oxidized to acetyl-CoA by pyruvate dehydrogenase (PDH).

The intensity of the D45 signal was about 5% that of the C2 multiplet indicating that the level of acetyl-CoA labeling was very low compared to that of oxaloacetate, pyruvate and PEP. However, since equations 4-9 explicitly assume zero labeling of acetyl-CoA, this small enrichment of acetyl-CoA could potentially introduce errors into the flux estimates. The possible impact of this on anaplerosis, pyruvate recycling, and gluconeogenic flux estimates was tested by simulating (using tcaSIM[1]) $^{13}$C NMR spectra of glutamine for two metabolic situations, one with no labeling of acetyl-CoA and another with entry of 5% [1,2-$^{13}$C$_2$]acetyl-CoA. Identical flux values (within 5%) were obtained by analysis of the resulting glutamate C2 multiplet areas using eqns 7-9. The enrichment of glutamate C4 at the level seen here in PAGN does not interfere with accurate measurement of the metabolic fluxes of interest.

Integration of Metabolic Data.

The relative flux values reported by the [U—$^{13}C_3$]propionate and $^2H_2O$ tracers were converted to absolute flux values by referencing them to GP as reported by turnover of [1,6-$^{13}C_2$]glucose. This provides the rather comprehensive picture of TCA cycle related fluxes and gluconeogenesis summarized in Table 2. Absolute flux estimates are reported for both glucuronate-based and PAGN-based $^{13}$C-isotopomer analyses.

The data in TABLE 2 are fluxes though pathways supporting glucose production. The results of deuterium NMR analysis were used to calculate the rate of glucose production from PEP and other sources. The rate of production of PEP from the TCA cycle (in triose units) was indexed to flux ratios (calculated from either urine acetaminophen glucuronide or urine phenylacetylglutamine) in the TCA cycle to calculate absolute fluxes. The numbers in parenthesis refer to the numbered pathways in FIG. 1. The abbreviation CS indicates citrate synthase.

These observations agree with GC-MS measurements of H5 and H2 enrichments in 14 hr and 18.5 hr fasted individuals where the contribution of gluconeogenesis to endogenous GP was reported to be 47±4% and 54±2%, respectively. Furthermore, the observation that $^2$H enrichment at H6S was about 95% that at H5 indicates the majority of gluconeogenic carbons are derived from the TCA cycle (PEP) and very little from glycerol. Most importantly, the $^2$H NMR spectrum of monoacetone glucose shows separate resonances for the prochiral H6 hydrogens of glucose while exchange of $^2H_2O$ at the level of fumarase in the TCA cycle specifically enriches the H6S position.

The capacity to measure individual enrichment of the prochiral glucose hydrogens by $^2$H NMR provides additional insight into the mechanisms that contribute to the enrichment of the methylene hydrogens of PEP from body water. While the exchange mechanisms for enriching H2 and H5 of glucose from body water are considered to be essentially quantitative, exchange of pyruvate and water hydrogens is believed to be only 80% complete.

If true, then enrichment of the PEP methylene hydrogens would be less than that of body water and the H6/H2 enrichment ratio of glucose as measured by GC-MS would underestimate the contribution of PEP to glucose production. However, this should only be true for glucose H6R

TABLE 2

| subject | Glucose production µmol/kg/min (1) | Rate of production of glucose from each source (µmol hexose/kg/min) | | | Fluxes from analysis of urine acetaminophen glucuronide (µmol/kg/min) | | | Fluxes from analysis of urine phenylacetyl glutamine (µmol/kg/min) | | |
|---|---|---|---|---|---|---|---|---|---|---|
| | | Glycogen (2) | glycerol (3) | PEP (4) | OAA → PEP (5) | PEP → pyruvate (6) | CS (7) | OAA → PEP (5) | PEP → pyruvate (6) | CS (7) |
| A | 9.8 | 5.59 | 0.00 | 4.21 | 38.69 | 30.32 | 5.85 | 80.62 | 72.25 | 12.25 |
| B | 10.0 | 5.50 | 0.60 | 3.90 | 25.02 | 17.22 | 3.38 | 54.90 | 47.10 | 8.65 |
| C | 10.7 | 4.60 | 0.11 | 5.99 | 37.88 | 25.90 | 6.89 | 65.77 | 53.79 | 10.70 |
| D | 12.1 | 5.45 | 0.73 | 5.93 | 47.12 | 35.26 | 6.27 | 75.11 | 63.25 | 11.04 |
| E | 11.0 | 6.49 | 0.33 | 4.18 | 38.55 | 30.19 | 4.52 | 67.54 | 59.18 | 11.93 |
| Mean | 10.7 | 5.52 | 0.35 | 4.84 | 37.45 | 27.78 | 5.38 | 68.79 | 59.11 | 10.91 |
| s.d. | 0.9 | 0.67 | 0.31 | 1.03 | 7.92 | 6.77 | 1.42 | 9.79 | 9.52 | 1.41 |

One aspect of the present invention provides a comprehensive metabolic profile of gluconeogenesis and TCA cycle activity in humans with three stable isotope tracers and NMR analysis of blood and urine samples. Multiple tracers are required because multiple experimental determinations are necessary to describe the known pathways involved in gluconeogenesis.

The measurements were obtained after enrichment of total body water with $^2H_2O$ and two $^{13}$C tracers, [1,6-$^{13}C_2$] glucose to measure endogenous glucose production and [U—$^{13}C_3$]propionate as an index of TCA cycle activity.

$^2$H NMR of monoacetone glucose.

Figure 7:
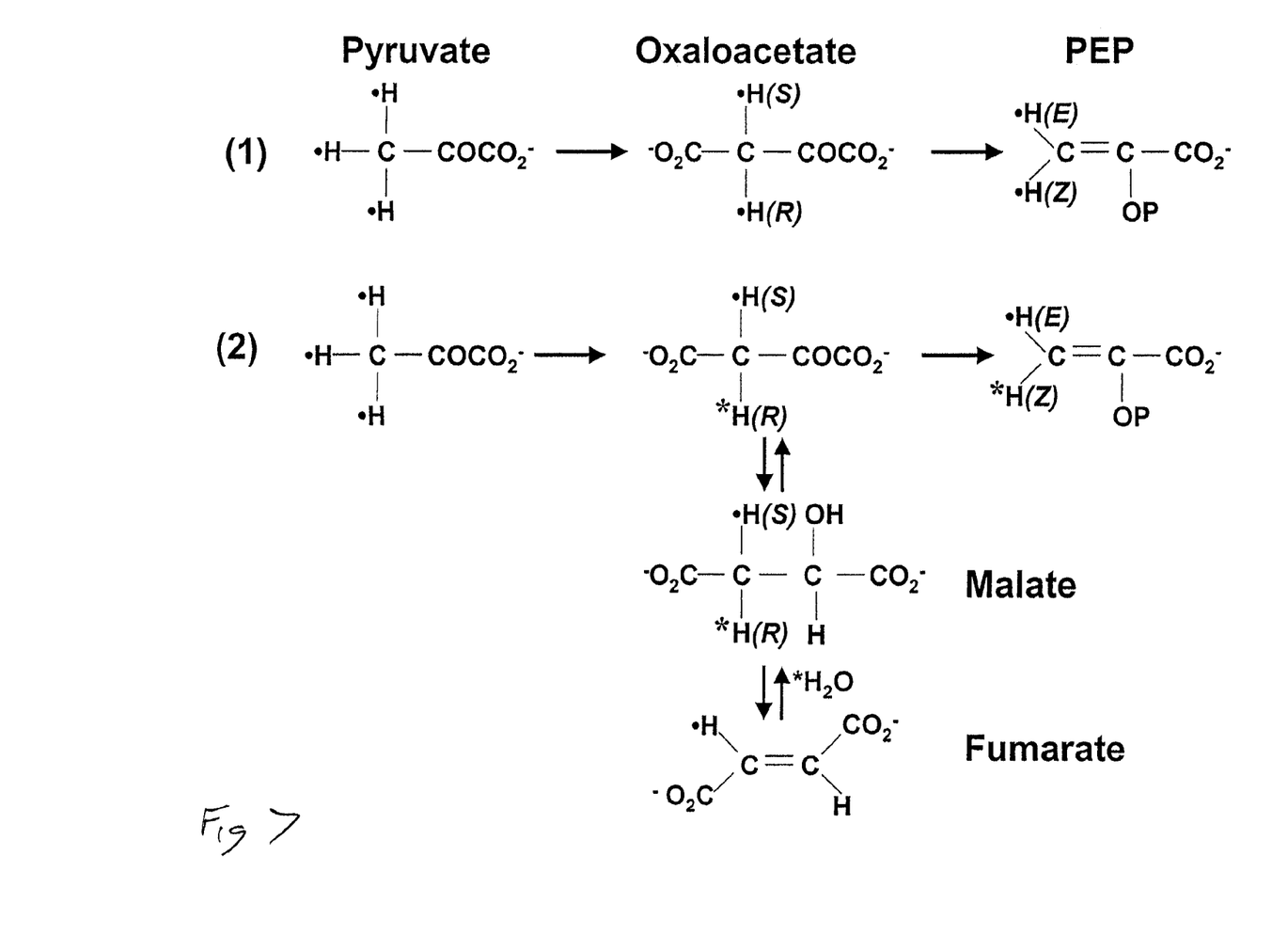
FIG. 7 depicts the labeling of PEP protons consistent with the present invention.

The $^2$H NMR spectrum of monoacetone glucose (42) derived from 20 mL of plasma glucose provided a convenient, direct measure of $^2$H-enrichment at each site in the glucose molecule. Enrichment at H2, reflecting isotopic equilibration of plasma glucose H2 with body water, was highest in every sample while enrichment at H5 was about 50% that at H2. This indicates that glycogenolysis and gluconeogenesis contribute equally to endogenous glucose production after a 16-18 hr fast.

because pyruvate enrichment is reported by the pro-S hydrogen of oxaloacetate2 while the pro-R hydrogen of this intermediate can undergo complete exchange with body water by interconversion with malate and fumarate (FIG. 7). If randomization between oxaloacetate, malate and fumarate is complete, then $^2$H-enrichment at the pro-R hydrogen of oxaloacetate would equal that of body water.

Thus, to the extent that randomization is incomplete, enrichment of the pro-R hydrogen of oxaloacetate will be a weighted average of pyruvate and body water enrichments. It is found that glucose H6R and H6S had near-equivalent levels of 2H-enrichment from $2H_2O$. This finding indicates that the H6/H2 enrichment ratio reported by GC-MS (a single H6 measurement is taken and a $^2$H enrichment distributed equally between H6R and H6S is assumed) should be equivalent to the H6S/H2 ratio reported by $^2$H NMR.

TCA cycle fluxes.

In this study, PEP-ck and pyruvate recycling fluxes were about 7- and 5-fold higher than TCA cycle flux while net gluconeogenic outflow (defined as PEP→glucose flux) was about 2-fold greater than TCA cycle flux. Compared to 24-28 hr fasted individuals, gluconeogenic outflow in the present group (16-18 hr fasted) tended to be lower while PEP-ck and pyruvate recycling fluxes tended to be higher.

Estimates of relative PEP→glucose flux show a large variation between different studies. In the study of Magnusson et al., PEP→glucose flux was reported to be approximately 3 times citrate synthase flux for both 60 hr fasted individuals and overnight-fasted subjects given I.V. glucose and glucagon. In comparison, the values reported by Diraison et al. are only ~0.5 times flux through citrate synthase.

Absolute TCA cycle fluxes are derived by indexing relative fluxes to an independent measurement of absolute PEP→glucose flux, therefore uncertainties in relative PEP→glucose flux propagate systematic uncertainties in estimates of absolute TCA cycle fluxes. For example, absolute hepatic citrate synthase fluxes estimated by Diraison, et al range from 20-35 μmol/kg/min, while estimates[3] from Magnusson, et al range from 5-7 μmol/kg/min. Absolute citrate synthase flux estimates from our study (5.4 μmol/kg/min and 10.9 μmol/kg/min from urinary glucuronate and PAGN, respectively), are in a similar range to the estimates of Magnusson, et al. There are no other published estimates of human hepatic citrate synthase flux available for comparison.

The anaplerotic, PEP recycling and TCA cycle fluxes reported here are based on a simple set of equations that are valid when excess enrichment of acetyl-CoA and carbons 4 and 5 of PAGN are negligible relative to enrichment carbons 1-3. The advantage of such equations over computational analysis is that they provide a simple and direct way of relating the C2 multiplet pattern from the $^{13}$C NMR spectrum of glucose or PAGN to metabolic fluxes through anaplerotic, recycling and oxidative pathways.

While the relative enrichments of PAGN carbon 4 encountered in the current study were sufficiently low for the simple equations to be valid, there may be circumstances where the relative enrichment of carbon 4 is high enough to introduce significant errors into metabolic flux estimates derived by this method. For example, in 60 hr fasted subjects infused with [3-$^{14}$C] lactate, the specific activity of carbon 4 relative to carbons 2 and 3 of PAGN was substantially higher compared to that found in subjects infused with either [2-$^{14}$C]propionate or [3-$^{14}$C]propionate.

In overnight fasted subjects infused with [3-$^{13}$C] lactate, excess enrichment in carbon 4 of PAGN was 35-42% of that found in carbons 2 and 3. Based on these results, it is likely that a [U—$^{13}$C$_3$]lactate tracer might also generate more enriched acetyl-CoA and a higher relative enrichment of PAGN C4 than [U—$^{13}$C$_3$]propionate under the same physiological conditions.

Such conditions generate more complex isotopomer distributions and require computational analysis for obtaining metabolic flux estimates. The labeling discrepancies between propionate and lactate tracers reflect heterogeneous metabolism of these substrates within the hepatic lobule. Given that propionate is quantitatively extracted from the portal circulation while lactate is not, it is probable that most of the propionate tracer is metabolized by the highly gluconeogenic periportal cells.

Consequently, the perivenous cells are exposed to little [U—$^{13}$C$_3$]propionate tracer directly, but are likely to encounter secondary labeled products of periportal [U—$^{13}$C$_3$]propionate metabolism, such as $^{13}$C-enriched glucose or lactate.

Analytical Considerations

A minimum of 20 mL of whole blood was required for the $^2$H NMR measurements of plasma glucose under conditions where total body water is enriched to ~0.5% in $^2$H. While this amount of blood can be safely collected from adults, this volume would be excessive for small children. Thus, for an equivalent study in children, one would be required to either increase the NMR sensitivity by going to smaller volume $^2$H microprobes or cryo-probes or collect larger amounts of glucose equivalents via urinary glucuronide.

What is claimed:

1. A method for preparing a tracer composition comprising:
   obtaining a $^{13}$C labeled Krebs cycle metabolite precursor that will produce an analyte; and
   obtaining a deuterium source,
   wherein gluconeogenesis is measured from a subject that was provided the precursor and the deuterium source, and produced the analyte, by comparison of relative nuclear magnetic resonance signal areas in a spectrum obtained from labeled components in the analyte.

2. The method of claim 1, wherein the analyte is $^{13}$C-glucose.

3. The method of claim 1, wherein the precursor is glucose, lactose, lactate or alanine.

4. The method of claim 1, wherein the deuterium source is deuterated water.

5. The method of claim 1, wherein the analyte is glucose deuterated in the 2, 5 and 6S positions, and any transformation in glucose that maintains the 2,5 and 6 positions in relation to one another.

6. The method of claim 1, wherein the analyte is (1-6 $^{13}$C$^2$)-glucose.

7. The method of claim 4, wherein the deuterated water is D$^2$O.

8. The method of claim 1, wherein nuclear magnetic resonance profiles are used to measure flux selected from the group consisting of pyruvate recycling, anaplerotic, gluconeogenic, and combinations thereof.

9. The method of claim 1, wherein the analyte is $^{13}$C-labeled glucose with the label at the 2 or 5 positions, or at both positions.

10. The method of claim 9, wherein the metabolite is a transformation of the labeled glucose containing the labeled 2 position, or the labeled 5 position, or both.

11. The method of claim 1, further comprising the step of adding [$^{13}$C$^3$] propionate.

12. The method of claim 1, wherein the Krebs cycle precursor is selected from the group consisting of pyruvic acid, acetic acid, acetoacetic acid and beta-hydroxybutyric acid.

13. The method of claim 1, wherein the analyte is selected from the group consisting of pyruvic acid, acetic acid citric acid, isocitric acid, cis-aconitic acid, 2-ketoglutaric acid, succinic acid, fumaric acid, malic acid, oxaloacetic acid, and mixtures thereof.

14. A method for preparing a tracer composition comprising:
   obtaining a deuterium source,
   wherein gluconeogenesis is measured from a subject that was provided the deuterium source, and produced an analyte, by comparison of the relative nuclear magnetic resonance signal areas in a spectrum obtained from deuterium components in the analyte, wherein the analyte is selected from the group consisting of glucose deuterated in the 2, 5 and 6 positions and deuterated glucose with any transformation that maintains the 2,5 and 6 positions in relation to one another.

15. A method for preparing a tracer composition comprising:
obtaining a deuterium source,
wherein gluconeogenesis is measured from a subject that was provided the deuterium source, and produced an analyte, by comparison of the relative nuclear magnetic resonance signal areas in a spectrum obtained from deuterium components in the analyte, wherein the analyte is $(1\text{-}6^{13}C^2)$.glucose.

16. The method of claim 14, wherein nuclear magnetic resonance profiles are used to measure flux selected from the group consisting of pyruvate recycling, anaplerotic, gluconeogenic, and combinations thereof.

17. A method for preparing a tracer composition comprising:
obtaining a deuterium source;
wherein gluconeogenesis is measured from a subject that was provided the deuterium source, and produced an analyte, by comparison of the relative nuclear magnetic resonance signal areas in a spectrum obtained from deuterium components in the analyte, wherein the analyte is selected from the group consisting of pyruvic acid, acetic acid citric acid, isocitric acid, cis-aconitic acid, 2-ketoglutaric acid, succinic acid, fumaric acid, malic acid, oxaloacetic acid, and mixtures thereof.

18. A method for preparing an isotopic metabolic flux tracer composition comprising:
providing a $^{13}C$ labeled Krebs cycle metabolite precursor to a subject to produce an analyte;
obtaining a sample from the subject; and
measuring nuclear magnetic resonance signals of the sample to determine the rate of gluconeogenesis.

19. The method of claim 18, wherein the analyte is $^{13}C$-glucose.

20. The method of claim 18, wherein the analyte is glucose labeled with $^{13}C$ at positions 1 through 6, or combinations of two or more at any position.

21. The method of claim 18, wherein the analyte is $(1\text{-}6\ ^3C^2)$-glucose.

22. The method of claim 18, wherein the sample is from blood, urine or tissue extracts.

23. The method of claim 18, further comprising the step of providing the subject with $[^{13}C_3]$ propionate.

24. The method of claim 18, wherein the Krebs cycle precursor is selected from the group consisting of pyruvic acid, acetic acid, acetoacetic acid, beta-hydroxybutyric acid.

25. The method of claim 18, wherein the analyte is selected from the group consisting of pyruvic acid, acetic acid citric acid, isocitric acid, cis-aconitic acid, 2-ketoglutaric acid, succinic acid, fumaric acid, malic acid, oxaloacetic acid, and mixtures thereof.

26. The method of claim 18, wherein the $^{13}C$ Krebs cycle precursor is provided orally.

27. A method for preparing a tracer composition comprising:
obtaining a deuterium source;
wherein gluconeogenesis is measured from a subject that was provided the deuterium source, and produced an analyte, by comparison of the relative nuclear magnetic resonance signal areas in a spectrum obtained from deuterium components in the analyte, and
wherein the analyte is glucose deuterated in the 2, 5 and 6 positions, and any transformation of glucose that maintains the 2,5 and 6 positions in relation to one another, and
wherein the analyte is produced in the blood, urine or tissue.

28. The method of claim 1, wherein the analyte is produced in the blood, urine or tissue.

29. A method for preparing an isotopic metabolic flux tracer composition comprising:
providing a $^{13}C$ labeled Krebs cycle metabolite precursor to a subject to produce an analyte;
obtaining a sample from the subject; and
measuring nuclear magnetic resonance of labeled tracers in the sample to determine the rate of gluconeogenesis,
wherein the analyte is $^{13}C$-glucose.

30. The method of claim 15, wherein nuclear magnetic resonance profiles are used to measure flux selected from the group consisting of pyruvate recycling, anaplerotic, gluconeogenic, and combinations thereof.

31. The method of claim 17, wherein nuclear magnetic resonance profiles are used to measure flux selected from the group consisting of pyruvate recycling, anaplerotic, gluconeogenic, and combinations thereof.

* * * * *